United States Patent
Liao et al.

(10) Patent No.: US 8,675,996 B2
(45) Date of Patent: Mar. 18, 2014

(54) CATHETER RF ABLATION USING SEGMENTATION-BASED 2D-3D REGISTRATION

(75) Inventors: Rui Liao, Princeton Junction, NJ (US); Norbert Strobel, Heroldsbach (DE); Chenyang Xu, Berkeley, CA (US)

(73) Assignee: Siemens Aktiengesellschaft, Munich (DE)

(*) Notice: Subject to any disclaimer, the term of this patent is extended or adjusted under 35 U.S.C. 154(b) by 684 days.

(21) Appl. No.: 12/821,235

(22) Filed: Jun. 23, 2010

(65) Prior Publication Data
US 2011/0069063 A1 Mar. 24, 2011

Related U.S. Application Data

(60) Provisional application No. 61/229,391, filed on Jul. 29, 2009.

(51) Int. Cl.
*G06K 9/32* (2006.01)
*G06K 9/00* (2006.01)

(52) U.S. Cl.
USPC .................... 382/294; 382/128; 382/131

(58) Field of Classification Search
None
See application file for complete search history.

(56) References Cited

U.S. PATENT DOCUMENTS

| | | | | |
|---|---|---|---|---|
| 2005/0027193 | A1* | 2/2005 | Mitschke et al. | 600/427 |
| 2006/0036167 | A1* | 2/2006 | Shina | 600/433 |
| 2006/0188139 | A1* | 8/2006 | Khamene et al. | 382/130 |
| 2006/0262970 | A1* | 11/2006 | Boese et al. | 382/131 |
| 2008/0143707 | A1* | 6/2008 | Mitchell | 345/418 |
| 2009/0290771 | A1* | 11/2009 | Frank et al. | 382/128 |
| 2010/0061603 | A1* | 3/2010 | Mielekamp et al. | 382/128 |
| 2010/0061611 | A1* | 3/2010 | Xu et al. | 382/131 |
| 2010/0296709 | A1* | 11/2010 | Ostrovsky-Berman et al. | 382/128 |
| 2011/0019889 | A1* | 1/2011 | Gering et al. | 382/131 |

OTHER PUBLICATIONS

WebMD, Cardiac Catheterization, Last updated Sep. 13, 2007, <http://web.archive.org/web/20080924190030/http://www.webmd.com/heart-disease/cardiac-catheterization?page=3>.*
Inside Radiology, Contrast Medium: Gadolinium versus Iodine in patients with kidney problems, Stacy Goergen et al, Published May 1, 2009, <http://www.insideradiology.com.au/pages/view.php?T_id=54>.*
Sundar et al, A Novel 2D-3D Registration Algorithm for Aligning Fluoro Images with 3D Pre-op CT/MR Images, Mar. 10, 2006, Medical Imaging 2006: Visualization, Image-Guided Procedures, and Display, p. 760-766.*

* cited by examiner

*Primary Examiner* — John Pauls
*Assistant Examiner* — Gregory Lultschik
(74) *Attorney, Agent, or Firm* — Donald B. Paschburg; F. Chau & Associates, LLC (57) ABSTRACT

A method for registering a two-dimensional image of a cardiocirculatory structure and a three-dimensional image of the cardiocirculatory structure includes acquiring a three-dimensional image including the cardiocirculatory structure using a first imaging modality. The acquired three-dimensional image is projected into two-dimensions to produce a two-dimensional projection image of the cardiocirculatory structure. A structure of interest is segmented either from the three-dimensional image prior to projection or from the projection image subsequent to projection. A two-dimensional image of the cardiocirculatory structure is acquired using a second imaging modality. The structure of interest is segmented from the acquired two-dimensional image. A first distance map is generated based on the two-dimensional projection image and a second distance map is generated based on the acquired two-dimensional image. A registration of the three-dimensional image and the two-dimensional image is performed by minimizing a difference between the first and second distance maps.

20 Claims, 8 Drawing Sheets

CATHETER RF ABLATION USING SEGMENTATION-BASED 2D-3D REGISTRATION

CROSS-REFERENCE TO RELATED APPLICATION

The present application is based on provisional application Ser. No. 61/229,391, filed Jul. 29, 2009, the entire contents of which are herein incorporated by reference.

BACKGROUND OF THE INVENTION

1. Technical Field

The present disclosure relates to catheter ablation and, more specifically, to catheter RF ablation using segmentation-based 2D-3D registration.

2. Discussion of Related Art

Atrial fibrillation (AFIB) is a leading cause of stroke and one of the most common heart rhythm disorders. In addition to or in place of anti-arrhythmic drugs, cardiac surgery and external deregulation, AFIB may be treated using radio-frequency catheter ablation (RFCA). In FFCA, faulty electrical pathways within the heart may be destroyed by advancing a catheter into the patient's blood vessels, for example, though the femoral vein, internal jugular vein, or subclavian vein. The catheter may then be advanced towards the heart and high-frequency electrical impulses may be sent though the catheter to induce the arrhythmia, and then ablate (destroy) the abnormal tissue that is observed to be responsible for the arrhythmia.

In order to guide the process of finding the site of the abnormal tissue, modern cardiac mapping systems may be used to draw the heart as a 3D model and provide real-time electrical activation information. Such mapping systems include CARTO XP and EnSite NavX. In order to provide the accurate position of the pacing catheter, all of the above systems require special catheters that are much more expensive than normal catheters.

Alternatively, 2D X-ray fluoroscopy has been routinely used for cardiac catheterization. Fluoroscopy may be used to provide real-time monitoring of the procedure and catheter location visualization at reasonably low cost. However, without contrast agent injection, fluoroscopic images do not display the anatomic structures such as the atria, the ventricles, the aorta, and the pulmonary veins. In addition, 2D fluoroscopy generates projection images representing a simplification of the imaged 3D structures.

SUMMARY

A method for registering a two-dimensional image of a cardiocirculatory structure and a three-dimensional image of the cardiocirculatory structure includes acquiring a three-dimensional image including the cardiocirculatory structure using a first imaging modality. The acquired three-dimensional image is projected into two-dimensions to produce a two-dimensional projection image of the cardiocirculatory structure. A structure of interest is segmented either from the three-dimensional image prior to projection or from the projection image subsequent to projection. A two-dimensional image of the cardiocirculatory structure is acquired using a second imaging modality. The structure of interest is segmented from the acquired two-dimensional image. A first distance map is generated based on the two-dimensional projection image. A second distance map is generated based on the acquired two-dimensional image. A registration of the three-dimensional image and the two-dimensional image is performed by minimizing a difference between the first and second distance maps.

A method for providing real-time visualization of anatomical structure during an electrophysiology intervention includes acquiring a three-dimensional image including the cardiocirculatory structure using a single-frame imaging modality, projecting the acquired three-dimensional image into two-dimensions to produce a two-dimensional projection image of the cardiocirculatory structure, segmenting a structure of interest either from the three-dimensional image prior to projection or from the projection image subsequent to projection, acquiring a sequence of two-dimensional image frames of the cardiocirculatory structure using a real-time imaging modality, segmenting the structure of interest from a selected frame of the acquired two-dimensional image, generating a first distance map based on the two-dimensional projection image, generating a second distance map based on the selected frame of the acquired two-dimensional image, performing registration of the three-dimensional image and the two-dimensional image by minimizing a difference between the first and second distance maps, and continuously superimposing the acquired three-dimensional image over each frame of the sequence of two-dimensional image frames and displaying the superposition for use in guiding electrophysiology intervention.

A computer system includes a processor and a non-transitory, tangible, program storage medium, readable by the computer system, embodying a program of instructions executable by the processor to perform method steps for registering a two-dimensional image of a cardiocirculatory structure and a three-dimensional image of the cardiocirculatory structure. The method includes acquiring a three-dimensional image including the cardiocirculatory structure using a first imaging modality, projecting the acquired three-dimensional image into two-dimensions to produce a two-dimensional projection image of the cardiocirculatory structure, acquiring a sequence of two-dimensional image frames of the cardiocirculatory structure using a fluoroscope, selecting an image frame from the sequence of two-dimensional image frames by gating the sequence of two-dimensional image frames according to cardiac phase information corresponding to the acquisition of the three-dimensional image, removing background information and/or devices from the selected frame of the acquired two-dimensional image, generating a first distance map based on the two-dimensional projection image, generating a second distance map based on the background and device removed two-dimensional image selected frame, and performing registration of the three-dimensional image and the two-dimensional image by minimizing a difference between the first and second distance maps.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF THE DRAWINGS

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention seek to provide a system and method for providing real-time visualization of anatomical structures and particularly, to provide visual guidance for the performance of electrophysiology (EP) procedures such as radio-frequency catheter ablation (RFCA). Visual guidance may include an augmented view of the heart anatomies and may help medical practitioners to navigate to the targeted area. In order to provide enhanced structural detail that is beyond what can be observed using a fluoroscope while retaining the ability to update image data in real-time, high-resolution pre-operative CT and/or MR volumetric data may be fused with the intra-operative 2D fluoroscopy during the performance of EP procedures by rendering an overlay image from the 3D data under a given viewing direction.

Exemplary embodiments of the present invention may include a method for alignment of 3D atrial CT and/or MR volumes with 2D fluoroscopic images through automatic segmentation-based 2D/3D registration. 2D/3D registration for EP application is challenging due to the mismatch between the structures present in the CT volume and the fluoroscopic images. For example, the inserting devices (such as catheters) are typically only shown in the fluoroscopic images, while many vessels are typically only highlighted and hence visible in the CT and MR volume. Therefore simple application of intensity-based 2D-3D registration techniques may fail to provide adequate registration. Accordingly, exemplary embodiments of the present invention utilize a novel approach for registration of 3D image volume with 2D fluoroscopic images.

Figure 1:
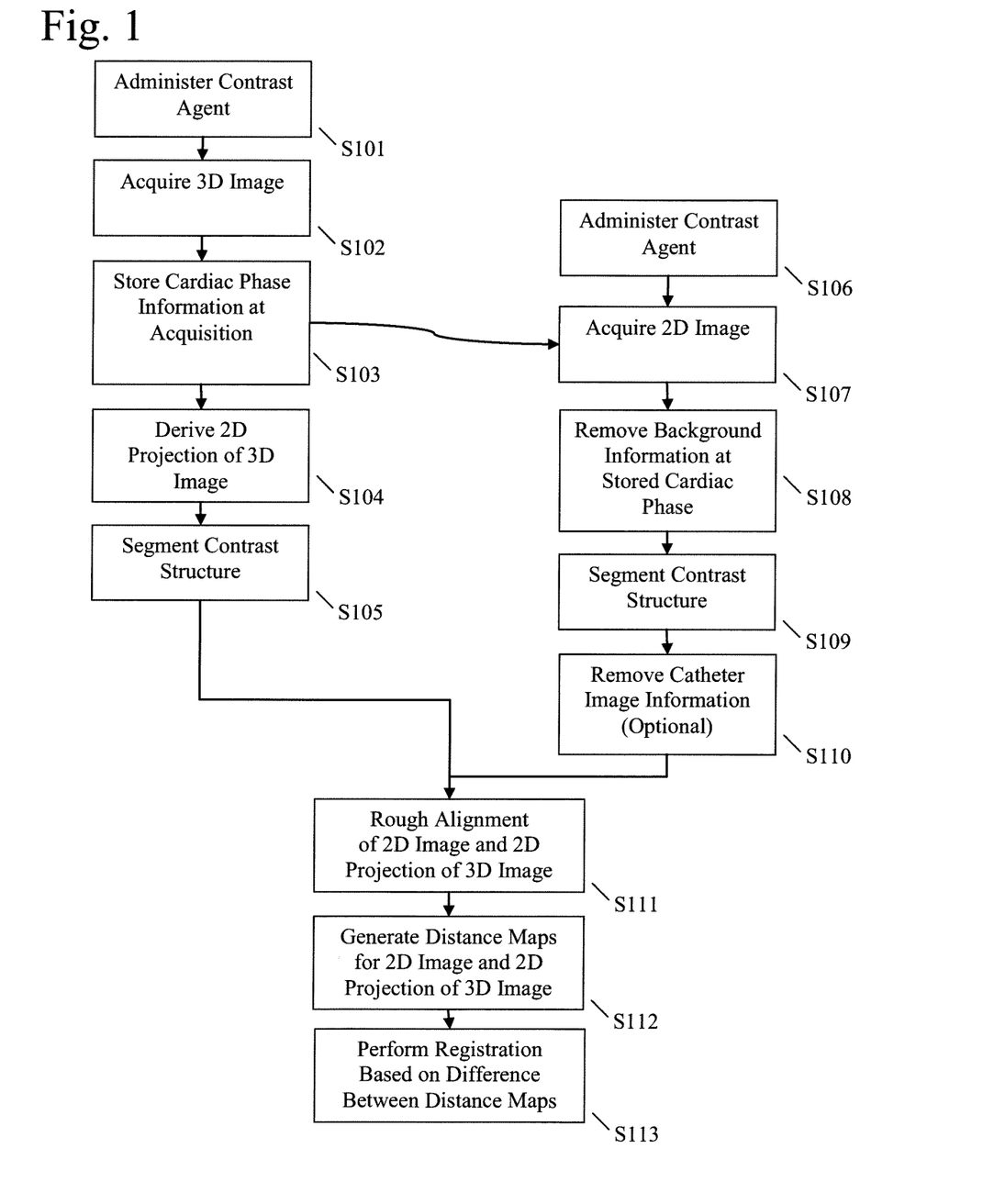
FIG. 1 is a flow chart for illustrating an approach to performing segmentation-based 2D/3D registration according to and exemplary embodiment of the present invention.

FIG. 1 is a flow chart for illustrating an approach to performing segmentation-based 2D/3D registration according to and exemplary embodiment of the present invention. First, data acquisition may be performed. Data acquisition may include administration of contrast agent (Step S101). The contrast agent used in this step may depend upon the modality used to acquire the three dimensional image data. For example, if the three dimensional image data is acquired using a CT scanner, the contrast may be radio contrast. However, if the three dimensional image data is acquired using an MR scanner, then contrast may be omitted or an appropriate contrast agent such as a gadolinium-based agent may be administered. After administration of the contrast agent (where desired), the three dimensional image data may be acquired (Step S102). As discussed above, the three dimensional image data may be acquired with one or more of a range of modalities such as CT and/or MR. This three dimensional image data may thereby be acquired pre-operatively. Alternatively, three dimensional image data may be acquired during the course of the operation through one or more circle runs of a C-arm CT system around the patient. After image acquisition (Step S102), the cardiac phase for the data acquisition may be registered and stored (Step S103). This information may be stored, for example, within a DICOM header for the 3D image data. Cardiac phase information may later be used to ensure that registration of the 3D image data to the intra-operative 2D image data is performed during a common point in the cardiac cycle. Similarly, breathing cycle information may be stored to later match breathing motion.

The 3D image data may then be projected into two dimensions (Step S104). The resulting 2D projection data may include a superposition of structures from various slices of the 3D image data. Accordingly, the 2D projection data may appear as a conventional x-ray image, even though it was derived from 3D image data. In deriving the 2D projection, an angle of projection may be selected that may best match the angle of the later-acquired intra-operative 2D image data. For example, the angle of projection may be selected to match that of the 2D fluoroscope that is prepared to acquire the intra-operative 2D image information. The projection angle may be based on the LAO/RAO and Cranual/Caudal angle. This angle may represent the orientation of the C-arm. For offline data (the case in which the 2D image data is saved as DICOM sequence and used for registration), this may be saved into the DICOM header. For online data (the case in which the 2D image data is acquired directly during the operation), the angle may be obtained directly from the system, for example, via TCP/IP communication.

Figure 2:
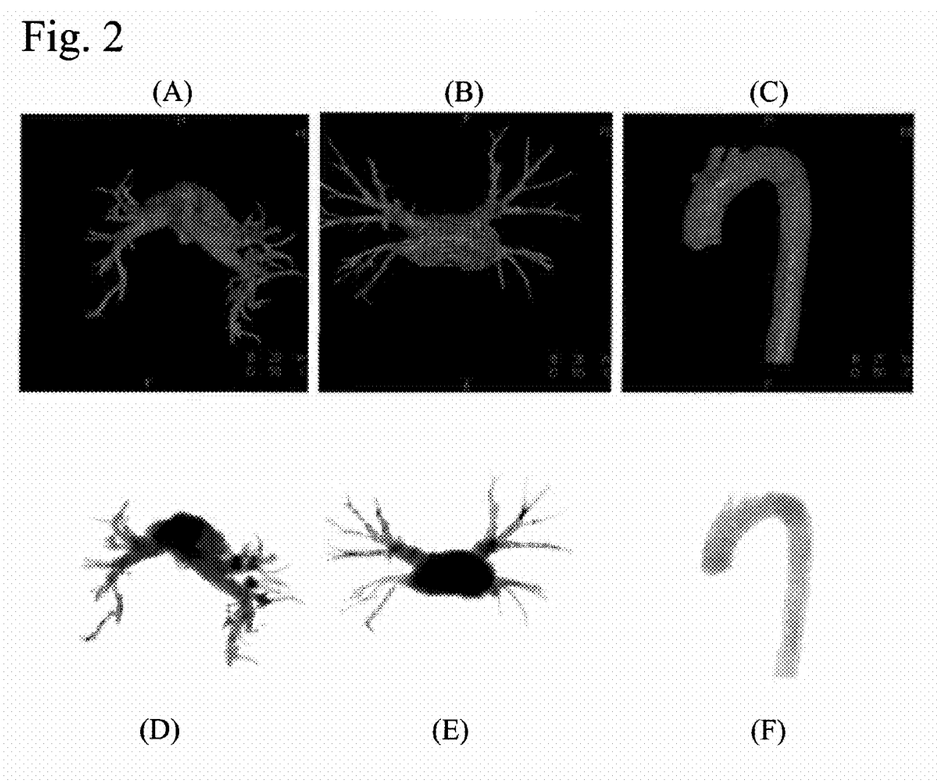
FIG. 2 is a series of images illustrating 2D projection according to exemplary embodiments of the present invention.

FIG. 2 is a series of images illustrating 2D projection according to exemplary embodiments of the present invention. FIG. 2(A) is a three-dimensional representation of a pulmonary artery while FIG. 2(D) is a projection of the pulmonary artery into two dimensions. Similarly, FIG. 2(B) is a three-dimensional representation of a pulmonary vein and left atrium while FIG. 2(E) is a projection of the pulmonary vein and left atrium into two-dimensions. Similarly, FIG. 2(C) is a three-dimensional representation of an aorta while FIG. 2(E) is a projection of the aorta into two-dimensions. The two dimensional projections may be generated using volume rendering techniques.

Segmentation may then be performed to identify contrast-highlighted organ(s) and or vessels (Step S105). Examples of structures to segment may include the pulmonary arteries, the aorta, the left atrium, and/or pulmonary veins. Segmentation may be performed either on the 3D image data or on the derived 2D projection data. Where segmentation is performed on the 3D image data, segmentation information may be carried forward to the derived 2D projection data. Where a contrast agent is not used in acquiring the 3D image data, structures of interest may still be segmented at this step without relying upon contrast highlighting. Segmentation may be performed either via manual punching of the image and/or through automatic segmentation. Automatic segmentation may be optionally followed by user-interactive editing.

Acquisition of the 2D image data may begin with administration of a contrast agent (Step S106). Where the 3D image data is acquired online, administration of the contrast agent at step S106 may coincide with the administration of the contrast agent at step S101. After contrast agent has been administered, the 2D image data may be acquired (Step S107). Acquisition of the 2D image may be performed using a fluoroscope. The 2D image may be acquired intra-operatively. As the 2D image data may be comprised of a series of frames captured to illustrate motion in real-time, registration of the 2D image data with the 2D projection data of the 3D image data may be performed at a common point in the cardiac cycle. To accomplish goal, the stored cardiac phase information pertaining to the 3D image acquisition may be retrieved and matched with real-time cardiac cycle information obtained from an ECG signal or estimate from the image frames to gate an appropriate 2D image frame for use in registration. Optionally, respiratory phase gating may similarly be used to provide an appropriate 2D image frame that matches both cardiac cycle and respiratory cycle of the acquired 3D image as closely as is practicable.

Background segmentation may then be performed to estimate and then remove background information from the selected 2D image frame (Step S108). Segmentation of the contrast-highlighted structure(s) may then be performed on the cardiac-gated and background removed image frame (Step S109).

Figure 3:
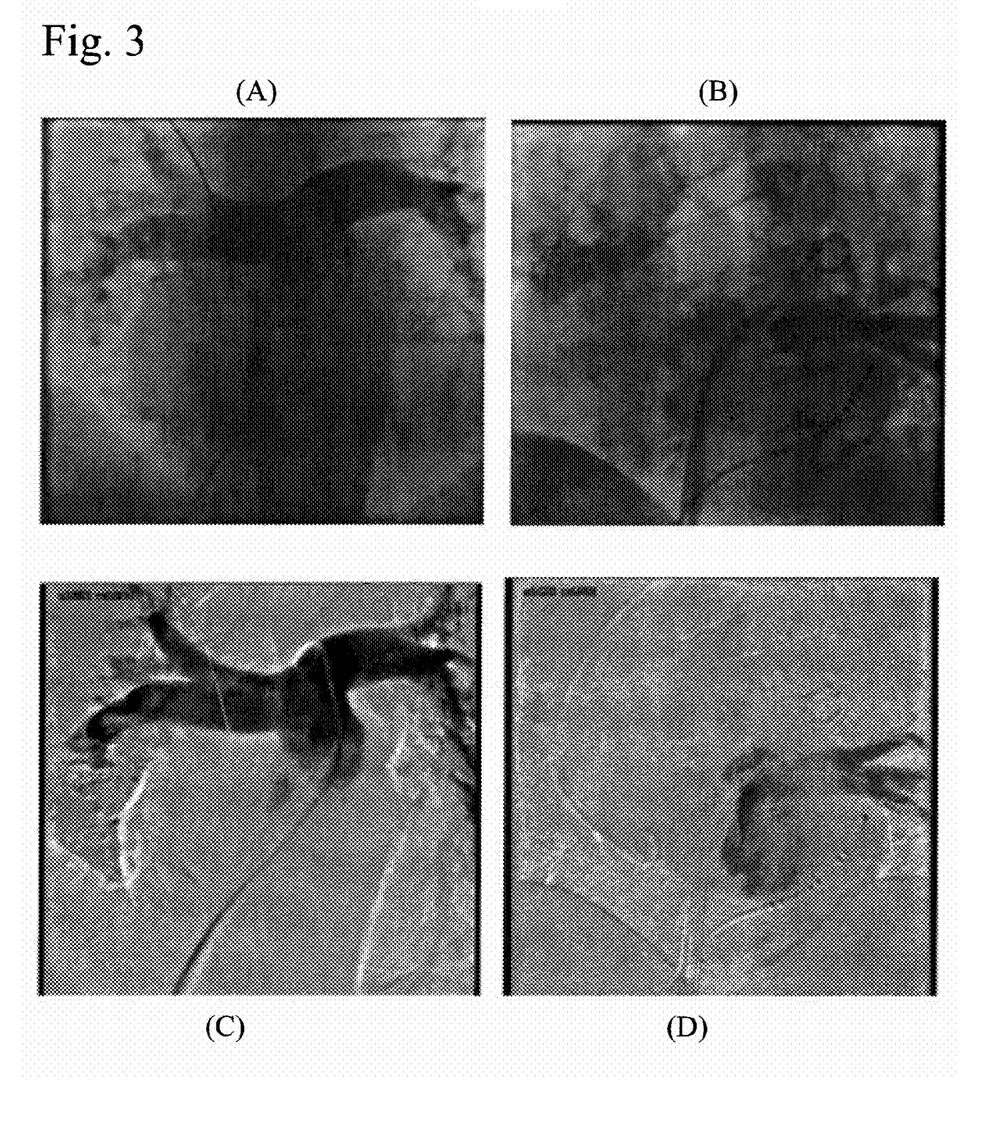
FIG. 3 is a set of images illustrating the effects of background subtraction according to exemplary embodiments of the present invention.

FIG. 3 is a set of images illustrating the effects of background subtraction according to exemplary embodiments of the present invention. FIG. 3(A) illustrates an original fluoroscope image frame including a pulmonary artery while FIG. 3(C) shows the same pulmonary artery after subtraction from the background. Similarly, FIG. 3(B) illustrates an original fluoroscope image frame including a pulmonary vein and left atrium while FIG. 3(D) shows the same pulmonary vein and left atrium after subtraction from the background. In these images, contrast-highlighted structures are shown. Digital radiography fill images are shown on the top row while associated subtracted images are shown on the bottom row. The associated subtracted images here are generated using DSA techniques.

Where the 2D image frame includes the image of one or more catheters or other intra-operative surgical implements, these implements may be removed from the 2D image frame (Step S110). Removal of image data corresponding to the catheter and/or other implements may facilitate subsequent registration as the pre-operative 3D image data will not have included catheter and/or other surgical implement image data.

Figure 4:
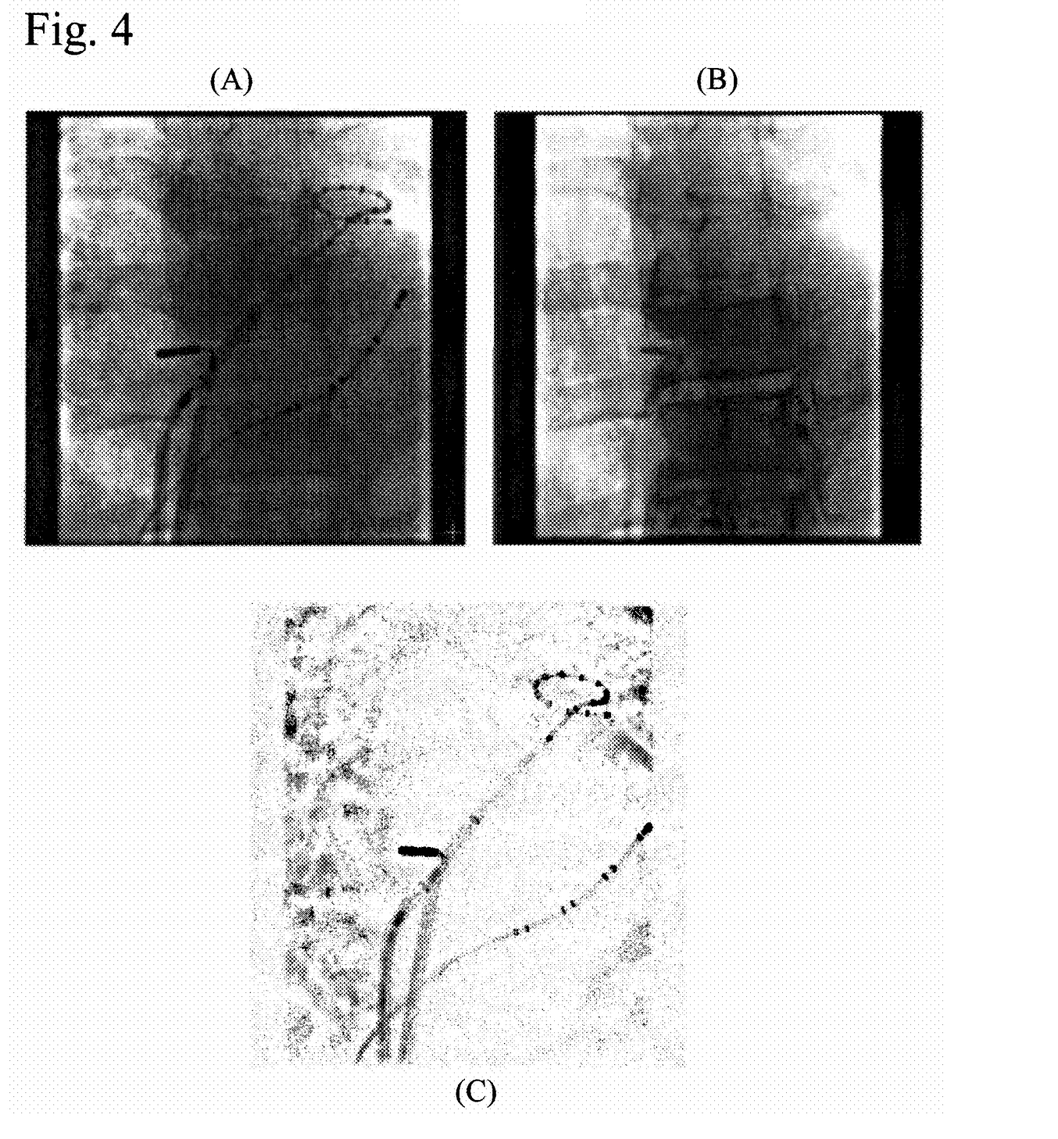
FIG. 4 is a set of images illustrating background estimation and implement extraction according to exemplary embodiments of the present invention.

FIG. 4 is a set of images illustrating background estimation and implement extraction according to exemplary embodiments of the present invention. FIG. 4(A) illustrates an original fluoroscope image frame. FIG. 4(B) illustrates the background estimation performed in accordance with step S108. FIG. 4(C) illustrates device extraction in accordance with Step S110.

Registration of the 2D and 3D image data may then be performed. Registration may begin with a rough alignment step in which the processed 2D image frame information is roughly aligned to the 2D projection of the 3D image data (Step S111). Rough alignment may be performed, for example, based on DICOM information from the 3D volume with respect to the internal coordinate system of the c-arm device. Distance maps may then be generated for both the processed 2D image frame and the 2D projection of the 3D image data (Step S112). In each distance map, each pixel of the image is labeled with the distance to the nearest image feature pixel. One example of a suitable feature pixel is a boundary pixel in a binary image. Here, a Euclidean distance transform algorithm may be used to compute the pixel distances for the distance maps. For discrete distance transform, a segmentation result is used to produce the binary image and accordingly, the rough alignment may be used in this regard. Alternatively, or additionally, a continuous distance map may be used. In such a case, explicit segmentation might not be needed, while proper normalization may be used on the intensity scale of the two continuous distance maps generated for the 2D image frame and for the 2D projection of the 3D image data.

Figure 5:
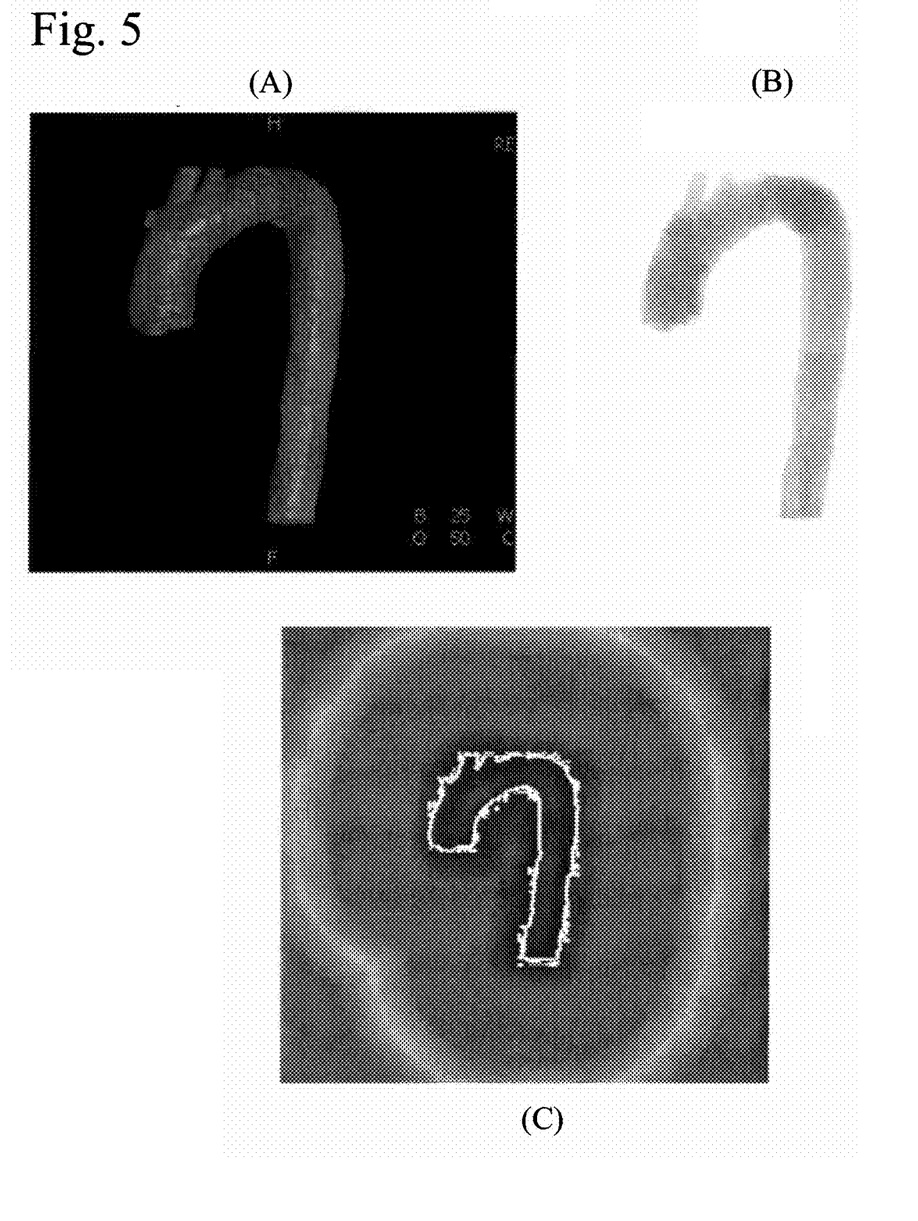
FIG. 5 is a set of sample images illustrating distance map generation of 3D image according to an exemplary embodiment of the present invention.

FIG. 5 is a set of sample images illustrating distance map generation of 3D image according to an exemplary embodiment of the present invention. In FIG. 5(A), 3D segmentation is shown. The segmented 3D structure is then projected into 2D as seen in FIG. 5(B). In FIG. 5(C), a distance map generated from the 2D projection of the 3D segmented image is shown.

Registration of the processed 2D image frame and the 2D projection of the 3D image data may be performed by computing a difference between the two distance maps and then minimizing the computed difference (Step S113). This calculation may be accomplished, for example, by the use of a proper function that can qualify the similarity between the two images, for example, by the sum of the absolute difference over the whole image, the normalized cross correlation, etc.

Figure 6:
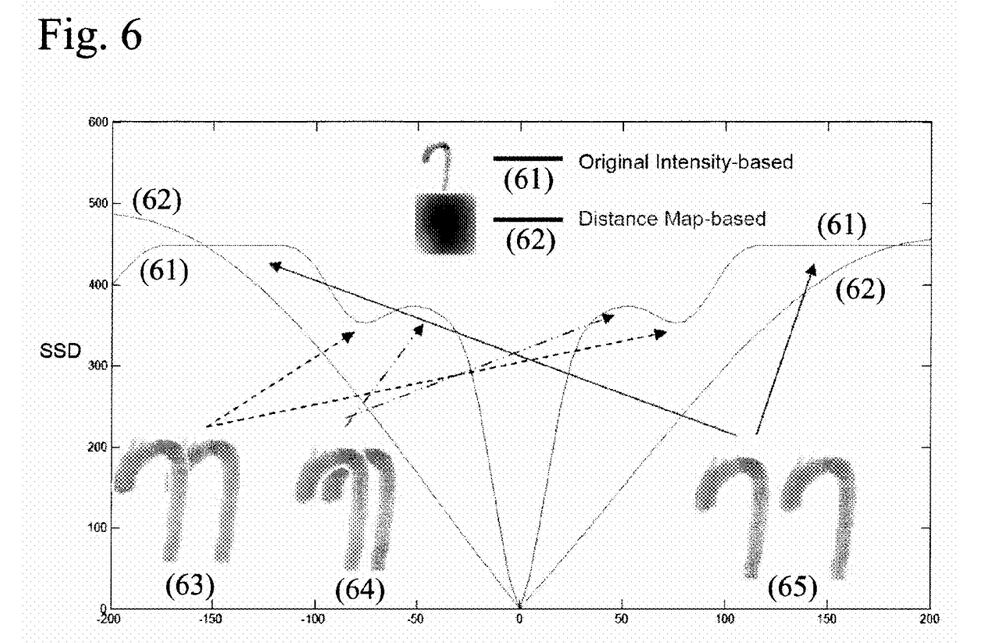
FIG. 6 is a graph comparing segmentation-based (distance map-based) 2D/3D registration as may be performed according to exemplary embodiments of the present invention against intensity-based registration.

FIG. 6 is a graph comparing segmentation-based (distance map-based) 2D/3D registration as may be performed according to exemplary embodiments of the present invention against intensity-based registration. Here, the sum of squared distance (SSD) is plotted against an offset between the reference image and the image to be registered. For the segmentation-based method involving distance map (62) the SSD cost function is shown as having a larger capture range and fewer local minima as compared to the intensity-based approach (61). The effects of local minima may be to provide poorly registered images, as can be seen at locations (63), (64), and (65) of the intensity-based approach (61). The reduction of local minima when using the distance map-based approach according to exemplary embodiments of the present invention may be the result of the smooth shape coding of the underlying structure which may effectively suppress "noise" generated by unrelated other structures.

Exemplary embodiments of the present invention, for example, as described above in detail, may be applied to any modality of volumetric data as long as the vessels and/or chambers can be segmented with sufficient accuracy, either semi-manually or automatically. Accordingly, the volumetric data may come from CT, MR, C-arm CT (e.g., syngo DynaCT Cardiac), PET etc. The registration may be primarily driven by the contours (the shape) of the segmented object, rather than its (gray-level) intensity values.

Exemplary embodiments of the present invention may have a large capture range that may be in part a result of the use of the two distance maps. As a distance map is a smooth shape coding of the underlying structure, the volumetric data may be reliably registered even if its rendered 2D representation is initially positioned far away from the registered position.

Exemplary embodiments of the present invention may be highly accurate due, at least in part, to the fact that the proposed vessels/chambers used for registration, i.e. pulmonary arteries, pulmonary veins, aorta, or left atrium, may be rich in geometric variations. In addition, segmentation of the vessels/chambers from both the 3D and 2D data may minimize the interference from other anatomic structures, leading to an accurate and reliable matching evaluation for a robust 2D-3D registration.

Exemplary embodiments of the present invention may use structures that are close to the target for registration, e.g., pulmonary veins for radio frequency catheter ablation of the antrum inside the left atrium. Therefore there may be no need to further compensate for the relative mismatch between the target and the registered organ for the pre-operative 3D data and intra-operative 2D fluoroscopy.

Exemplary embodiments of the present invention may take advantage of the temporal information contained in a fluoroscopy sequence for reliable extraction and enhancement of the contrast-highlighted organs in fluoroscopy.

The workflow described in detail above may minimize online operation in the interventional suite. Before the intervention an accurate and reliable segmentation of the vessels/chambers from the 3D volume can be obtained. For 3D data with inferior quality, interactive segmentation can be applied. Extraction and enhancement of the vessel/chamber from the 2D fluoroscopic images may be fully automatic so that no user interaction is needed during the intervention for the purpose of 2D/3D registration.

In EP cases, the inserted devices (e.g. catheters) may be visible in the fluoroscopic images. As discussed above with respect to step S110, image data corresponding to the inserted implements, such as catheters, may be removed in the 2D segmentation mask for reliable registration with a 3D image taken without any additional devices in place. This may be achieved using the following approach: Since the inserted devices are constantly moving during an EP procedure due to the cardiac motion, they are not visible in the estimated background image. The device can then be detected from a frame that is taken without contrast enhancement in the matching cardiac phase (at which the 3D volume was acquired). The detected device is then removed from the 2D segmentation mask by proper connected component and/or global geometry analysis and subtraction."

Moreover, if breathing motion is observed to be significant, respiratory-gating may be applied. This may be achieved, for example, using a surrogate respiratory signal or from a breathing motion estimate derived using image-based methods.

Rough alignment, as described above with respect to step S111 may be performed by registering the images using the spine, which may be prominently featured in both images. The spine can be extracted and/or enhanced from the 2D fluoroscopic sequence, for example, using techniques similar to those described above with respect to background detection, which may explore temporal information contained in a fluoroscopic sequence. Minimization of the distance maps may then be used for fine adjustment to compensate for the offset between the heart and the spine for the pre-operative 3D volume and the intra-operative fluoroscopy.

Other landmarks, such as a circumferential (lasso) catheter, may be segmented in fluoroscopy images and also matched to the corresponding structure in the forward projected 3D segmentation mask (surface, landmark etc) using segmentation-based registration involving distance maps. This can further improve the robustness of the proposed method, especially when there is mismatch between the segmented 2D and 3D, e.g., caused by incomplete filling of contrast in the fluoroscopy scene.

Biplane images or two monoplane images taken from two different views may be used in place of the two-dimensional fluoroscope image frames to further constrain the registration for higher accuracy and robustness.

Figure 7:
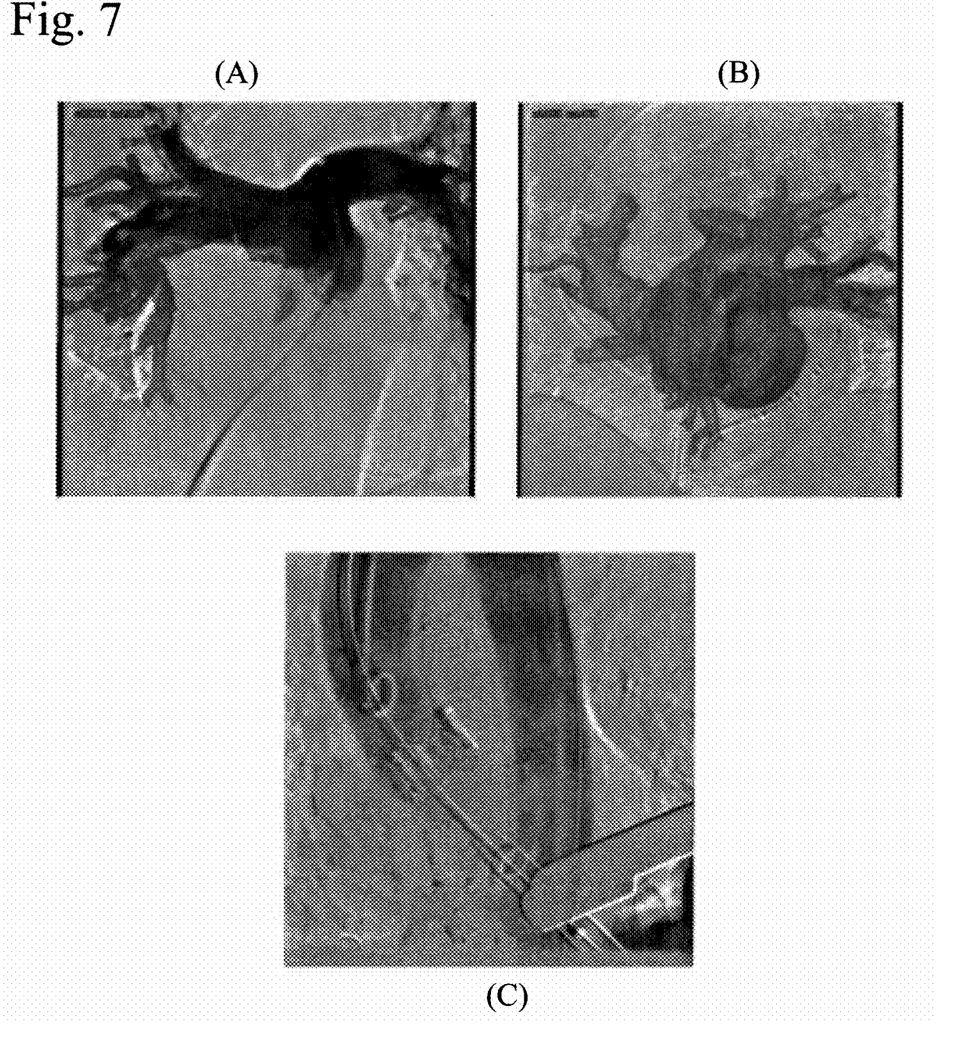
FIG. 7 is a set of images illustrating segmentation-based 2D/3D registration involving distance maps according to exemplary embodiments of the present invention.

FIG. 7 is a set of images illustrating segmentation-based 2D/3D registration involving distance maps according to exemplary embodiments of the present invention. Here, segmentation-based registration is applied to various structures such as the pulmonary artery in FIG. 7(A), the pulmonary vein and left atrium in FIG. 7(B), and the aorta in FIG. 7(C).

Figure 8:
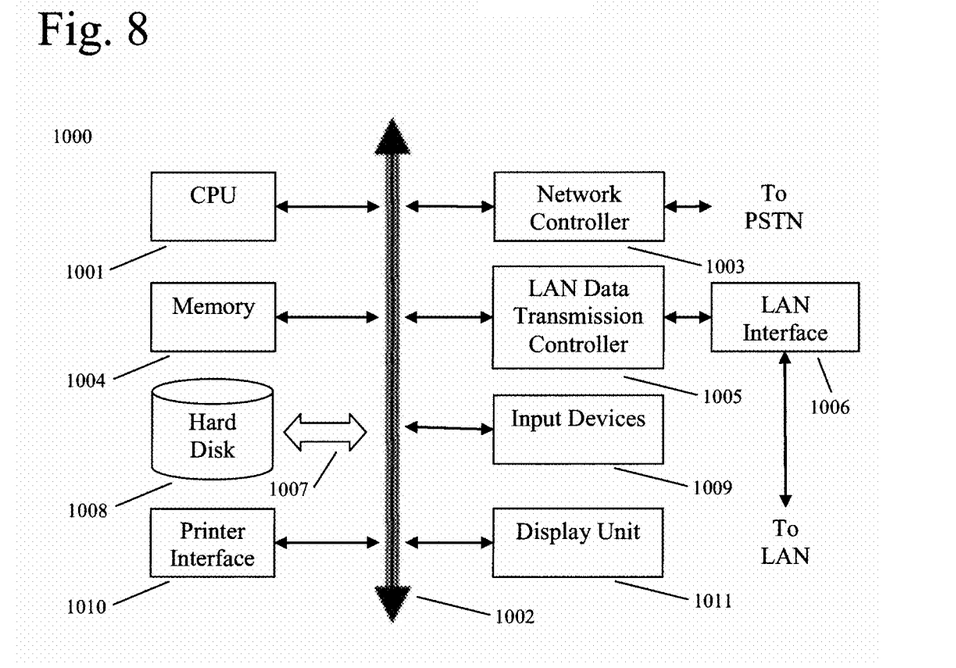
FIG. 8 shows an example of a computer system capable of implementing the method and apparatus according to embodiments of the present disclosure.

FIG. 8 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A method for registering a first two-dimensional image of a cardiocirculatory structure and a three-dimensional image of the cardiocirculatory structure, comprising:
    acquiring the three-dimensional image including the cardiocirculatory structure using a first imaging modality;
    projecting the acquired three-dimensional image into two-dimensions to produce a two-dimensional projection image of the cardiocirculatory structure;
    segmenting a structure of interest either from the acquired three-dimensional image or from the two-dimensional projection image;
    acquiring the first two-dimensional image of the cardiocirculatory structure using a second imaging modality;
    segmenting the structure of interest from the acquired first two-dimensional image;
    generating a first distance map based on the two-dimensional projection image in which each pixel of the two-dimensional projection image is labeled with a distance to a nearest image feature pixel of the two-dimensional projection image;
    generating a second distance map based on the acquired first two-dimensional image in which each pixel of the acquired first two-dimensional image is labeled with a distance to a nearest image feature pixel of the acquired first two-dimensional image; and
    performing registration of the acquired three-dimensional image and the acquired first two-dimensional image by minimizing a difference between the first and second distance maps, wherein each of the above steps are performed using a computer system.

2. The method of claim 1, wherein a contrast agent is administered prior to the acquisition of the three-dimensional image and segmenting a structure of interest either from the acquired three-dimensional image or from the two-dimensional projection image includes segmenting a contrast-enhanced structure.

3. The method of claim 1, wherein a contrast agent is administered prior to the acquisition of the first two-dimensional image and segmenting the structure of interest from the acquired first two-dimensional image includes segmenting a contrast-enhanced structure.

4. The method of claim 1, wherein cardiovascular phase information, corresponding to a moment in which the three-dimensional image is acquired, is stored and used to ensure that the acquired first two-dimensional image used in registration represents a comparable cardiac phase with respect to the acquired three-dimensional image.

5. The method of claim 1, wherein background information is removed from the first acquired two-dimensional image prior to the performance of registration.

6. The method of claim 1, wherein catheter information is removed from the acquired first two-dimensional image prior to the performance of registration.

7. The method of claim 1, wherein the first imaging modality is a CT scan or an MRI.

8. The method of claim 1, wherein the second imaging modality is a fluoroscope and the acquired first two-dimensional image includes a sequence of image frames acquired in real-time.

9. The method of claim 1, wherein a rough alignment of the two-dimensional projection image and the acquired first two-dimensional image is performed prior to the generation of the first and second distance maps.

10. The method of claim 9, wherein the rough alignment includes performing rough registration based on an image of a spine within the two-dimensional projection image and the acquired first two-dimensional image.

11. The method of claim 1, wherein in projecting the acquired three-dimensional image into two-dimensions, an angle of projection is selected based on an angle of acquisition for the acquired first two-dimensional image.

12. The method of claim 1, wherein the structure of interest includes pulmonary arteries, an aorta, a left atrium, or pulmonary veins.

13. The method of claim 1, wherein for each of the first and second distance maps, pixel distances are calculated using a Euclidean distance transformation.

14. The method of claim 1, wherein minimizing the difference between the first and second distance maps includes qualification of a similarity between the two distance maps by a sum of absolute difference or normalized cross correlation.

15. A method for providing real-time visualization of an anatomical structure during an electrophysiology intervention, comprising:
   acquiring a three-dimensional image including the anatomical structure using a single-frame imaging modality;
   projecting the acquired three-dimensional image into two-dimensions to produce a two-dimensional projection image of the anatomical structure;
   segmenting a structure of interest either from the acquired three-dimensional image or from the two-dimensional projection image;
   acquiring a sequence of two-dimensional image frames of the anatomical structure using a real-time imaging modality;
   segmenting the structure of interest from a selected frame of the acquired sequence of two-dimensional image frames;
   generating a first distance map based on the two-dimensional projection image in which each pixel of the two-dimensional projection image is labeled with a distance to a nearest image feature pixel of the two-dimensional projection image;
   generating a second distance map based on the selected frame of the acquired sequence of two-dimensional image frames in which each pixel of the selected frame of the acquired sequence of two-dimensional image frames is labeled with a distance to a nearest image feature pixel of the selected frame of the acquired sequence of two-dimensional image frames;
   performing registration of the acquired three-dimensional image and the sequence of two-dimensional image frames by minimizing a difference between the first and second distance maps; and
   continuously superimposing the acquired three-dimensional image over each frame of the sequence of two-dimensional image frames and displaying the superposition for use in guiding electrophysiology intervention,
   wherein each of the above steps are performed using a computer system.

16. The method of claim 15, wherein cardiovascular phase information corresponding to a moment in which the three-dimensional image is acquired is stored and used to select the selected frame of the acquired sequence of two-dimensional image frames.

17. The method of claim 15, wherein background information is removed from the selected frame of the acquired sequence of two-dimensional image frames prior to the performance of registration.

18. A computer system comprising:
   a processor; and
   a non-transitory, tangible, program storage medium, readable by the computer system, embodying a program of instructions executable by the processor to perform method steps for registering a two-dimensional image of a cardiocirculatory structure and a three-dimensional image of the cardiocirculatory structure, the method comprising:
   acquiring the three-dimensional image including the cardiocirculatory structure using a first imaging modality;
   projecting the acquired three-dimensional image into two-dimensions to produce a two-dimensional projection image of the cardiocirculatory structure;
   acquiring a sequence of two-dimensional image frames of the cardiocirculatory structure using a fluoroscope;
   selecting an image frame from the sequence of two-dimensional image frames by gating the sequence of two-dimensional image frames according to cardiac phase information corresponding to the acquisition of the three-dimensional image;
   removing background information from the selected image frame of the acquired sequence of two-dimensional image frames;
   generating a first distance map based on the two-dimensional projection image in which each pixel of the two-dimensional projection image is labeled with a distance to a nearest image feature pixel of the two-dimensional projection image;
   generating a second distance map based on the background-removed selected image frame of the acquired sequence of two-dimensional image frames in which each pixel of the background-removed selected image frame of the acquired sequence of two-dimensional image frames is labeled with a distance to a nearest image feature pixel of the background-removed selected image frame of the acquired sequence of two-dimensional image frames; and performing registration of the three-dimensional image and the acquired sequence of two-dimensional image frames by minimizing a difference between the first and second distance maps.

19. The computer system of claim 18, wherein the first imaging modality is a CT scan or an MRI.

20. The computer system of claim 18, wherein a rough alignment of the two-dimensional projection image and the background-removed selected image frame of the acquired sequence of two-dimensional image frames is performed prior to the generation of the first and second distance maps.

\* \* \* \* \*